(12) United States Patent
Honda

(10) Patent No.: US 7,626,163 B2
(45) Date of Patent: Dec. 1, 2009

(54) DEFECT REVIEW METHOD AND DEVICE FOR SEMICONDUCTOR DEVICE

(75) Inventor: Toshifumi Honda, Yokohama (JP)

(73) Assignee: Hitachi High-Technologies Corporation, Tokyo (JP)

(*) Notice: Subject to any disclaimer, the term of this patent is extended or adjusted under 35 U.S.C. 154(b) by 95 days.

(21) Appl. No.: 12/033,470

(22) Filed: Feb. 19, 2008

(65) Prior Publication Data

US 2008/0290274 A1 Nov. 27, 2008

(30) Foreign Application Priority Data

Mar. 30, 2007 (JP) ............................. 2007-090197

(51) Int. Cl.
*H01J 37/28* (2006.01)
*H01J 37/256* (2006.01)
*G01N 23/04* (2006.01)

(52) U.S. Cl. ........................ 250/306; 250/307; 250/310; 250/311; 250/492.2; 250/492.22; 250/492.3

(58) Field of Classification Search ................. 250/306, 250/307, 310, 311, 492.2, 492.22, 492.3
See application file for complete search history.

(56) References Cited

U.S. PATENT DOCUMENTS 7,109,483 B2 * 9/2006 Nakasuji et al. ............. 250/310

2007/0145270 A1 * 6/2007 Miyamoto et al. .......... 250/310
2008/0121804 A1 * 5/2008 Nakasuji et al. ............. 250/310
2009/0010527 A1 * 1/2009 Honda et al. ................ 382/149
2009/0058437 A1 * 3/2009 Honda et al. ................ 324/751

FOREIGN PATENT DOCUMENTS

JP 10-135288 5/1998
JP 2002-033365 1/2002

* cited by examiner

*Primary Examiner*—Nikita Wells
(74) *Attorney, Agent, or Firm*—Antonelli, Terry, Stout & Kraus, LLP.

(57) ABSTRACT

A defect review method and device of the invention solves the previous problem of a long inspection time that is caused by the increase of a process-margin-narrow pattern as a result of the size reduction of a semiconductor device. With the method and device of the invention, an SEM (Scanning Electron Microscope) image is derived by capturing an image of a process-margin-narrow pattern portion extracted based on lithography simulation with image-capturing conditions of a relatively low resolution. The resulting SEM image is compared with CAD (Computer Aided Design) data for extraction of any abnormal section. An image of the area extracted as being abnormal is captured again, and the resulting high-resolution SEM image is compared again with the CAD data for defect classification based on the feature amount of the image, e.g., shape deformation. The abnormal section is then measured in dimension at a position preset for the classification result so that the time taken for inspection can be prevented from increasing.

16 Claims, 14 Drawing Sheets

103: DETAILED INSPECTION/REVIEW POINT

FIG.3
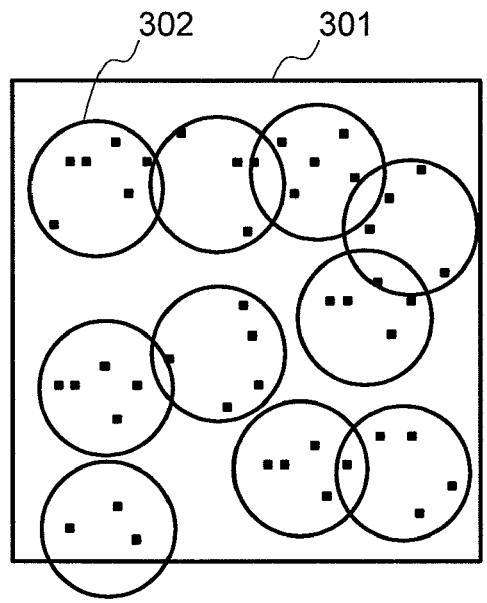
FIG.4
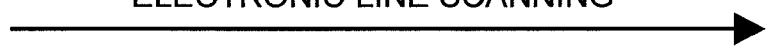
DIRECTION OF ELECTRONIC LINE SCANNING
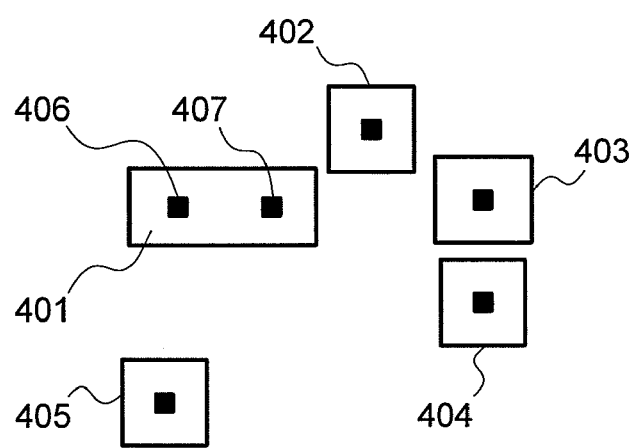

FIG.19
(a) 1901: NORMAL
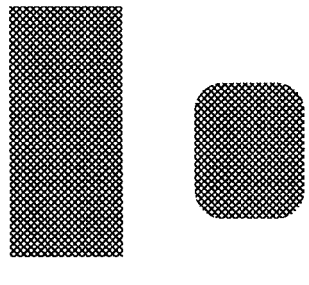
(b) 1902: THICKNESS INCREASED
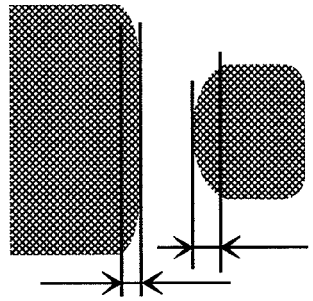
(c) 1903: THICKNESS REDUCED
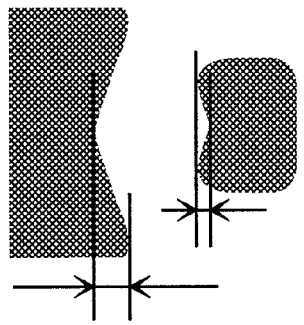
(d) 1904: THIN BRIDGE
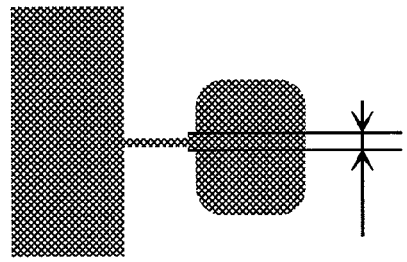
(e) 1905: THICK BRIDGE
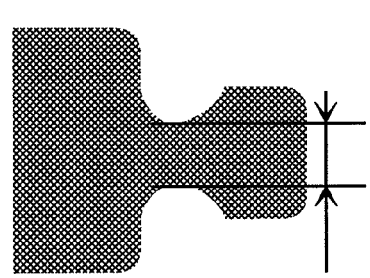
(f) 1906: BROKEN
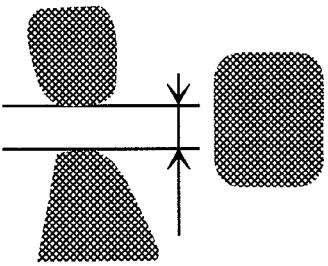
(g) 1907: FOREIGN SUBSTANCE
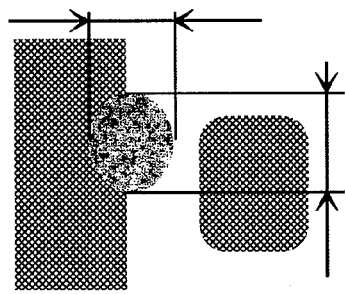

DEFECT REVIEW METHOD AND DEVICE FOR SEMICONDUCTOR DEVICE

CLAIM OF PRIORITY

The present application claims priority from Japanese application Ser. No. JP2007-090197, filed on Mar. 30, 2007, the content of which is hereby incorporated by reference into this application.

BACKGROUND OF THE INVENTION

The present invention relates to a scanning electron microscope (hereinafter, SEM) that captures an image of a review target through detection of electrons emitted from a part of an industry product, especially a semiconductor being in a semiconductor wafer process irradiated with converged electron beams and, more specifically, to a defect review method and device for a semiconductor device that reviews in detail any defect detected by an SEM-type semiconductor wafer inspection device and an SEM-type semiconductor pattern measurement device both required to capture an image of high magnification, and a semiconductor wafer to go through more detailed inspection based on the defect detected by these inspection devices.

As a semiconductor is reduced in size, control over the wafer manufacturing process is getting difficult more and more for the semiconductor. In the exposure process for the semiconductor, a difference of pattern size caused by optical proximity effects becomes not negligible, i.e., between the design pattern and the pattern transferred to a resist. In consideration thereof, optical proximity correction (OPC) has been performed through simulation of the optical proximity effects for correcting a mask pattern. In the exposure process of using an OPC-applied mask, the spots where deficiencies are often caused with a relative ease due to the process variation i.e., hot spots.

In such hot spots, the layout design change has been recently popular for the mask to be normally manufactured without being susceptible to any process variation of some level if occurred. Such mask designing for suppressing any possible deficiency during manufacturing is getting popular as DFM (Design For Manufacturing), and for performing DFM with efficiency, a demand is growing for a system that can smoothly feed back the state of manufacturing to designing. To meet such a demand, as described in Patent Document 1 (JP-A-2002-33365), there is a method for automatically determining a point of managing the state of manufacturing through analysis of CAD (Computer Aided Design) data, and an image of this position is captured using a microscope such as SEM (Scanning Electron Microscope) for review use.

There is another method in Patent Document 2 (JP-A-10-135288) for managing the state of manufacturing through reviewing of defects with a high magnification using a review apparatus including a microscope such as SEM. The defects are those detected through inspection of a wafer entirely or partially.

SUMMARY OF THE INVENTION

Such previous technologies, however, are not good enough anymore for monitoring the state of manufacturing of a semiconductor wafer with the sufficient level of correctness. That is, with the method of Patent Document 1, i.e., the method for automatically determining a point for managing the state of manufacturing through analysis of CAD data, the number of such points becomes too large to estimate, thereby resulting in a difficulty in controlling all of the points. This is due to the density increase of a semiconductor pattern, and the size increase of a semiconductor wafer from 200 to 300 mm. In consideration thereof, an attempt has been made to reduce the number of points for estimation by sampling of an estimating wafer or chip, but no such method as leading to the maximum effects with the smallest number of sampling is yet established.

Moreover, the review apparatus of Patent Document 2 also has a problem of a difficulty in reviewing any target defect. For DFM, information of importance for manufacturing is whether satisfactory agreement is observed between the hypothesis of lithography simulation at the time of designing and the result of inspection and measurement during actual manufacturing. As such, reviewing only defects having little to do with designing, e.g., random foreign substances, causes a difficulty of feedback to designing.

Information of importance for feedback to designing is derived by defects such as size reduction or increase observed to a pattern, the diameter reduction observed to a contact hole, and others. With a general device for inspecting the appearance of a wafer, any defects not to be detected unless with considerably high sensitivity for defect detection will be DOI (Defect of Interest). On the other hand, if the inspection device is considerably increased in sensitivity as such, a large number of non-DOI defects will be detected, e.g., detected are non-defective grains on wiring pattern surface or difference of film thickness between dies of comparison use. As such, there is a problem of not being able to appropriately manage the state of manufacturing.

An object of the invention is to solve such problems observed in the previous technologies, and to provide a method and apparatus for inspecting or reviewing semiconductor defects with an efficiency of inspecting a large number of DOI defects at high speed.

In order to achieve the object as such, in the invention, in a method of automatically determining a point of managing the state of manufacturing through analysis of CAD data, a low-magnification image in the vicinity of an inspection point is captured with first image-capturing conditions using an SEM, and from the resulting SEM image, an abnormal section is extracted by comparison with CAD data. The SEM is then set with second image-capturing conditions, thereby capturing only a high-magnification SEM image of the abnormal section suited for reviewing.

That is, a first aspect of the invention is directed to a method for reviewing any defect on an inspection target sample using a scanning electron microscope, including the steps of: grouping a plurality of reviewing inspection areas on the inspection target sample; capturing an image of each of the reviewing inspection areas grouped using the scanning electron microscope being under first image-capturing conditions, and acquiring a plurality of images of the reviewing inspection areas with a first magnification; extracting an abnormal section from the acquired images of the inspection areas by comparison with design data; and capturing an image of the extracted abnormal section using the scanning electron microscope being under second image-capturing conditions, and acquiring an image of the extracted abnormal section with a second magnification being higher than the first magnification.

A second aspect of the invention is directed to a method for reviewing any defect on an inspection target sample using a scanning electron microscope, including the steps of: capturing images of a plurality of reviewing inspection areas on the inspection target sample to allow all of the inspection areas to fit in an electronic line scanning range of the scanning electron microscope being under first image-capturing conditions, and acquiring a plurality of images of the reviewing inspection areas; extracting an abnormal section from the images of the inspection areas acquired by image capturing with the first image-capturing conditions by comparison with design data; and capturing an image of the extracted abnormal section using the scanning electron microscope being under second image-capturing conditions, and acquiring an image of the abnormal section.

A third aspect of the invention is directed to a method for reviewing any defect on an inspection target sample using a scanning electron microscope, including the steps of: fitting a plurality of inspection areas on the inspection target sample in an electronic line scanning range of the scanning electron microscope, and capturing an image of each of the inspection areas with first image-capturing conditions; extracting, by comparison with design data, an abnormal section from the images of the inspection areas acquired by image capturing with the first image-capturing conditions; capturing an image of the extracted abnormal section using the scanning electron microscope being under second image-capturing conditions; classifying the image of the abnormal section being a result of image capturing with the second image-capturing conditions based on a result of comparison with the design data; measuring a size of a portion preset for every type of classification based on a result of classification; and displaying the result of classification and a result of size measurement together with the captured images.

A fourth aspect of the invention is directed to a defect review apparatus for a semiconductor device, including: a scanning electron microscope provided with a table that is allowed to move in a plane with an inspection target sample placed thereon; image-capturing condition setting means for setting image-capturing conditions for reviewing the inspection target sample using the scanning electron microscope; table control means for controlling the table of the scanning electron microscope to allow a plurality of reviewing inspection areas on the inspection target sample to fit in an image capturing area of the scanning electron microscope being under first image-capturing conditions set by the image-capturing condition setting means; first image processing means for extracting, by comparison with design data, an abnormal section from images of the inspection areas acquired by the scanning electron microscope being under the first image-capturing conditions set by the image-capturing condition setting means; and second image processing means for processing an image of the extracted abnormal section in a state that the scanning electron microscope is set with second image-capturing conditions by the image-capturing condition setting means.

A fifth aspect of the invention is directed to a defect review apparatus for a semiconductor device, including: scanning electron microscope means; image-capturing condition setting means for setting image-capturing conditions for reviewing an inspection target sample using the scanning electron microscope means; first image processing means for extracting, by comparison with design data, an abnormal section from images of a plurality of inspection areas on the inspection target sample acquired in a state that the scanning electron microscope means is set with first image-capturing conditions by the image-capturing condition setting means; and second image processing means for processing an image of the abnormal section extracted by the first image processing means in a state that the scanning electron microscope means is set with second image-capturing conditions by the image-capturing condition setting means, and measuring a size of a portion preset for every type of classification based on a classification result of the abnormal section.

According to the aspects of the invention, with the first image-capturing conditions, electron beams for scanning use by an SEM are set large in current amount, and the resulting inspection can be performed at high speed compared with direct inspection under the second image-capturing conditions.

Further, according to the aspects of the invention, the frequency of moving a stage can be reduced. As such, with the first image-capturing conditions, the electron beams are so set as to be small in aperture angle on an inspection target for the aim not to cause a large change of diameter thereof on the target at a position away from the axis of an SEM and a position on the axis. This accordingly enables to inspect a plurality of inspection areas without moving the stage to move the position of an inspection target so that the resulting inspection can be performed at high speed.

Still further, according to the aspects of the invention, at a position away from the axis of an SEM, together with two deflectors disposed in an objective lens in the direction away from an inspection object, a third deflector is disposed in or below the objective lens. This is aimed to virtually move the objective lens so that the diameter of electron beams is prevented from increasing at the position away from the axis of the SEM.

Still further, according to the aspects of the invention, at the time of comparison between CAD data and an SEM image, an abnormal section is extracted with each different criterion depending on the portion of design data, i.e., a line portion and a corner portion so that the resulting extraction can be implemented with stability.

These and other objects, features and advantages of the invention will be apparent from the following more particular description of preferred embodiments of the invention, as illustrated in the accompanying drawings.

BRIEF DESCRIPTION OF THE DRAWINGS

FIG. 3 is a plan view of a semiconductor chip showing exemplary grouping in a circular area for determining a position of moving a stage to enable image capturing at the time of inspection;

FIG. 4 is a plan view of a semiconductor chip showing an exemplary area for scanning by electron beams;

FIG. 19A is an SEM image as a result of image capturing of a normal pattern with a high resolution;

FIG. 19B is an SEM image as a result of image capturing of a thick pattern with a high resolution;

FIG. 19C is an SEM image as a result of image capturing of a thin pattern with a high resolution;

FIG. 19D is an SEM image as a result of image capturing of a thin bridge pattern with a high resolution;

FIG. 19E is an SEM image as a result of image capturing of a thick bridges pattern with a high resolution;

FIG. 19F is an SEM image as a result of image capturing of a broken pattern with a high resolution;

FIG. 19G is an SEM image as a result of image capturing of a foreign substance with a high resolution;

DESCRIPTION OF THE PREFERRED EMBODIMENTS

Embodiments of the invention are described by referring to FIGS. 1 to 20C.

In today's circumstances where very-small graphics on a chip are of almost the same size as an exposure wavelength, the optical proximity correction (OPC) with a consideration given to the optical proximity effects of lights is being essential for a mask pattern. To be specific, in consideration of the phenomenon of diffraction of light, for example, the mask pattern is required to be additionally provided with a pattern for correction use at a corner portion of the graphic thereon or others. Such a mask pattern shows thereon some variation, e.g., some portion easily suffers from defects and some not, due to varying process even with any same pattern pitch.

Such a portion where easily suffering from defects is referred to as hot spot, and any portion where being easily susceptible to varying process due to lithography simulation or others can be identified on CAD data. Some design change is required to be made to reduce the number of hot spots, and for such change making, there needs to estimate any possible alienation between the hypotheses at the time of designing by lithography simulation or others and the actual circumstances.

In consideration thereof, for implementation, it is important to mainly inspect the pattern corresponding to the hot spot, and manage the state of manufacturing thereof. The finer pattern pitch accordingly leads to the reduction of the margin in the process conditions for formation of any normal pattern, thereby considerably increasing the number of the inspection areas to be managed.

Figure 1:
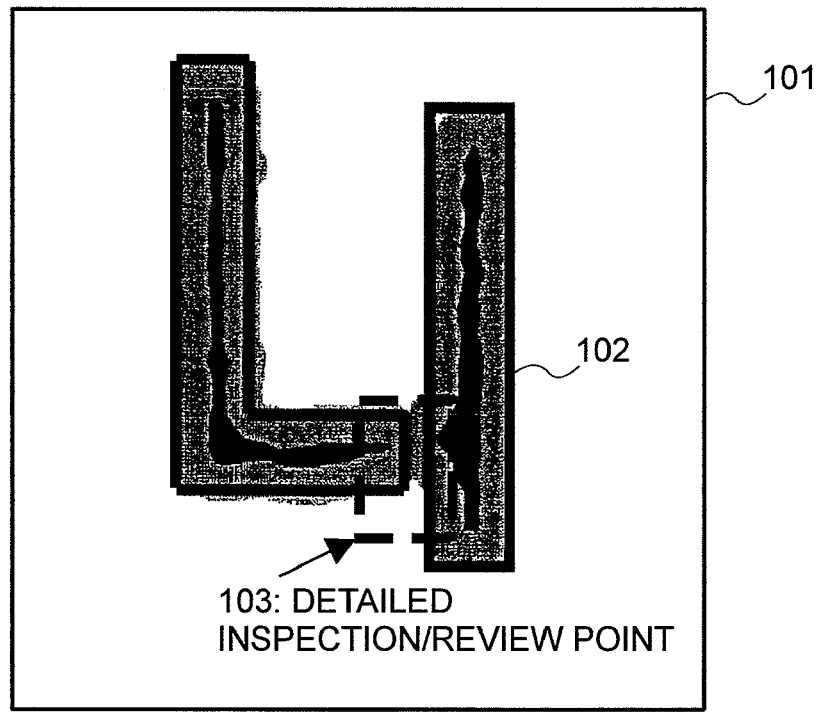
FIG. 1 is a plan view of a circuit pattern showing an exemplary inspection area.

For inspection corresponding to such a hot spot, a high-magnification image is acquired using an SEM for measurement of the width between patterns, for example. FIG. 1 shows an exemplary case where an SEM is used to capture an image of a hot spot and therearound. In FIG. 1, a reference numeral 101 denotes an SEM image, and a reference numeral 102 denotes design data, which is generally described with the combination of data of rectangular. Also in FIG. 1, a reference numeral 103 denotes an inspection area for reviewing, which is susceptible to process variation for pattern formation.

For determining the quality of a mask pattern or the process conditions, there needs to inspect a large number of inspection areas susceptible to process variation. With the previous technologies, however, this increases the time for inspection and measurement. The reasons of increasing the time for image capturing of an SEM image include the movement of a stage to move the field of view for SEM image capturing, and the time taken for an SEM to complete image capturing.

In consideration thereof, in the invention, the area for scanning by electron beams of an SEM is increased in size for the aim of reducing the movement frequency of a stage.

Figure 2:
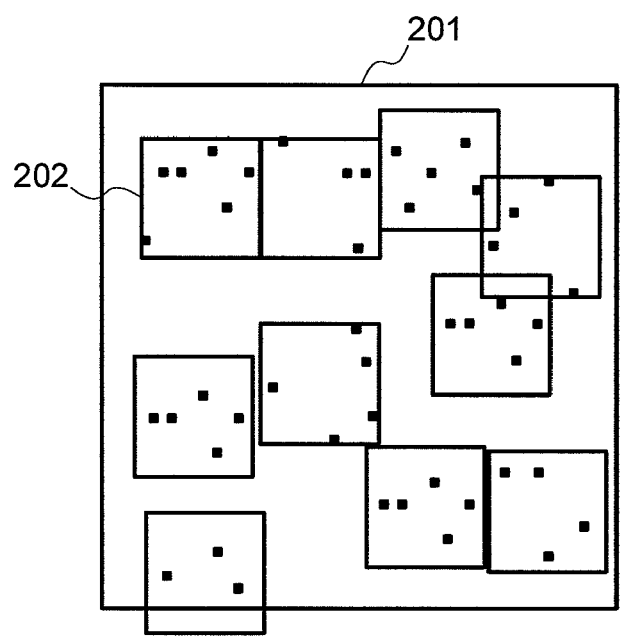
FIG. 2 is a plan view of a semiconductor chip showing exemplary grouping in a rectangular area for determining a position of moving a stage to enable image capturing at the time of inspection.

FIG. 2 shows inspection points on a wafer chip. In FIG. 2, a reference numeral 201 denotes a semiconductor chip, and the chip carries therein a plurality of inspection areas. The chip is of the size of about 4 mm, and the area available for scanning by electron beams of an SEM of this invention is of the size about several tens to hundreds of μm. It means, to acquire SEM images of inspection areas scattering on the entire surface of the semiconductor chip, there needs to move the stage for a plurality of times. In consideration thereof, as shown in FIG. 2, grouping is performed to rectangular-shaped inspection areas 202 available for scanning by electron beams without moving the stage.

The electron beams are increased in diameter on an inspection target by the area to be irradiated with the electron beams moving away from the center axis of the SEM, and by frame aberration, for example. Such diameter increase determines the confines of the area available for scanning by electron beams. The aberration is determined by the distance from the axis so that, unlike FIG. 2, setting the circular inspection areas 302 for scanning as in FIG. 3 enables grouping with more appropriateness. Note here that, in view of the time taken for such grouping, grouping of rectangular areas as FIG. 2 is more efficient.

For the purpose of reducing the time for an SEM to complete image capturing, the area available for scanning by electron beams is not entirely subjected to image capturing but only an inspection area is subjected to scanning by electron beams. The concern here is that the positional deviation is caused at the time of scanning by electron beams, and thus the scanning by electron beams is not always accurate. As such, the inspection area is added with an offset estimated for such a positional deviation, and the resulting area is subjected to scanning by electron beams for capturing an SEM image. This offset is typically about 100 nm. Herein, the positional deviation of the part to be irradiated with electron beams is required to be corrected through positioning by comparison with CAD data, and it is thus considered preferable if the inspection areas are each provided with edges respectively in the directions of X and Y to enable positioning to the offset estimated for the positional deviation.

FIG. 4 shows an image capturing area for electron beams. In the drawing, reference numerals 401 to 405 each denote an image capturing area for an SEM. Also in the drawing, reference numerals 406 and 407 are each an inspection area adjacent to each other in the direction of scanning by electron beams, and these areas are rather simultaneously subjected to image capturing as exemplified by 401 in view of time reduction. On the other hand, when the inspection areas are similarly adjacent to each other but in the direction orthogonal to the scanning direction by the electron beams, as exemplified by 403 and 404, these inspection areas may be subjected to image capturing separately in view of time reduction. This is because, at the time of scanning by electron beams in an SEM, the blanking time is required to put the electron beams back to the scanning starting point from the scanning end point. Accordingly, when the inspection areas are disposed close to each other in the scanning direction by electron beams, even if the number of areas is increased to some degree for scanning by electron beams, scanning a large number of inspection areas by one-time scanning by electron beams can eventually lead to the shorter time for completing the scanning. As such, grouping is performed in consideration also of the direction of scanning by electron beams, and SEM image capturing is performed based thereon.

First Embodiment

By referring to FIGS. 5 to 16, a first embodiment is described below.

Figure 5:
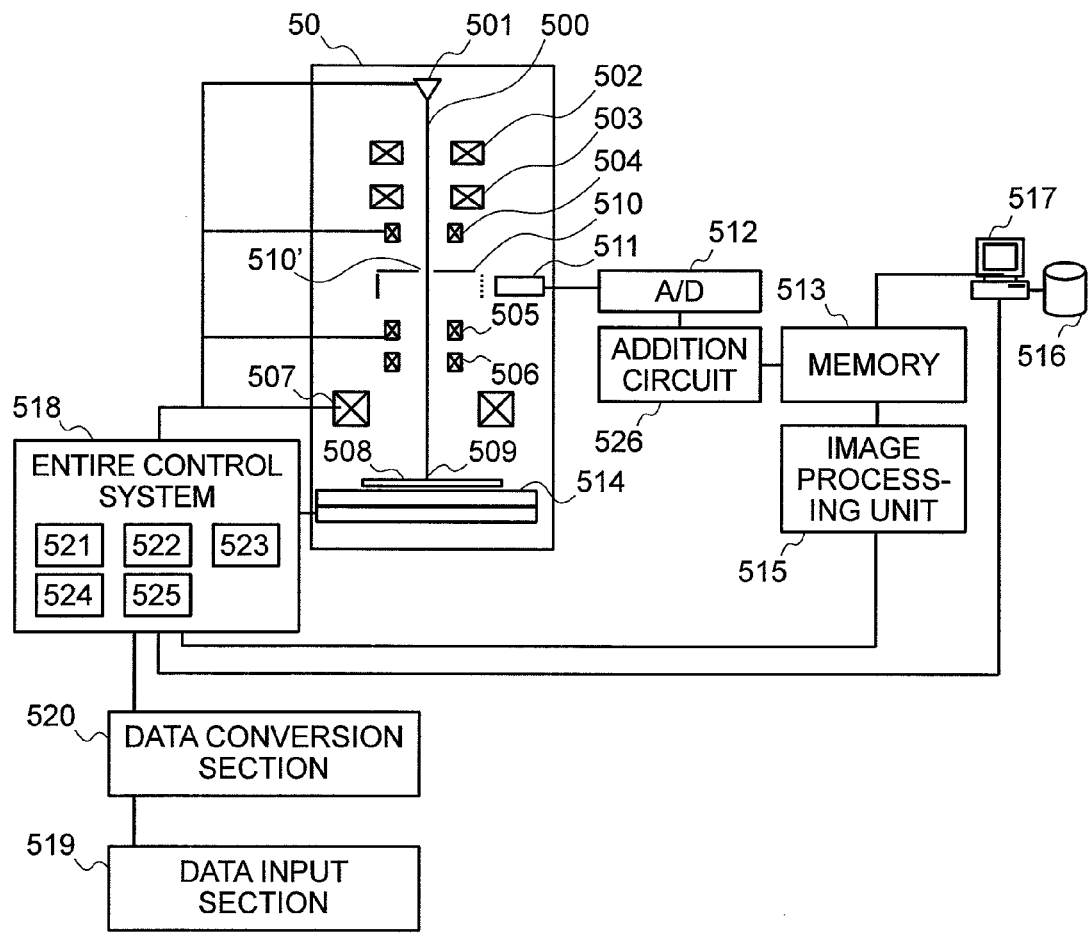
FIG. 5 is a block diagram showing the schematic configuration of an inspection device in its entirety of a first embodiment.

First of all, FIG. 5 shows the entire configuration of an inspection device for use in the first embodiment. Inside of an SEM body 50, an electro optical system and a detection system are provided as below. In FIG. 5, a reference numeral 501 denotes an electron source, from which electron beams 500 are emitted. The emitted electron beams 500 pass through electron lenses 502 and 503, and then are corrected with any astigmatism and misalignment by an electron beam axis adjuster 504.

In FIG. 5, reference numerals 505 and 506 denote deflectors provided in two stages, and are provided to deflect the electron beams 500 so that the irradiation position is controlled for the electron beams 500. The electron beams 500 are converged by an objective lens 507 before irradiation to an image capturing target area 509 of a wafer 508.

From the image capturing target area 509, the result, i.e., secondary electrons and the reflecting electrons, is emitted. The secondary electrons and reflecting electrons collide against a reflector plate 510 formed with a primary electron beam through hole 510', and the resulting secondary electrons are detected by an electron detector 511.

The secondary electrons and the reflecting electrons detected by the detector 511 are converted into digital signals by an A/D (Analog-to-Digital) converter 512, and the conversion result is stored in a memory 513. Note here that there is an addition circuit 526 disposed between the A/D converter and the memory.

When the electron beams 500 are used for scanning repeatedly to any one specific portion, the addition circuit 526 calculates an addition average, i.e., frame addition, for a detection signal being a result of beam irradiation at any specific one portion so that the shot noise can be favorably reduced. In the drawing, a reference numeral 514 denotes an XY stage, and is used to move the wafer 508 to enable image capturing at any arbitrary position of the wafer 508. Also in the drawing, a reference numeral 515 denotes an image processing unit, which extracts an absorption section from the images stored in the memory 513. The image processing unit 515 also measures the size of the area already extracted as the abnormal section or calculates the outer appearance of the image.

For extraction of the abnormal section, comparison of design data is possible. For such comparison, the image processing unit 515 is made ready for an input of CAD data or data being a conversion result thereof, and a comparison is made in terms of in-pattern edge interval between a pattern detected from an SEM image and a pattern corresponding thereto derived from the CAD data. When the difference of edge interval is larger than a preset reference value, the portion is extracted as an abnormal section.

Alternatively, a comparison may be made in terms of edge interval between an inspection target pattern derived from CAD data and a pattern corresponding thereto derived from an SEM image, and when the difference of edge interval is larger than a preset reference value, the portion may be extracted as an abnormal section.

Still alternatively, a comparison may be made in terms of edge position between an inspection target pattern derived from an SEM image and a pattern corresponding thereto derived from CAD data, and when the difference is larger than a preset reference position being a characteristic point on a sample, the portion may be extracted as an abnormal section.

Moreover, the image processing unit 515 finds the degree of matching between an SEM image and CAD data for correcting any positional deviation at the time of scanning by electron beams in an SEM. As an exemplary method therefor, a position where a normalized correlation value takes the maximum value may be calculated as a position where matching is observed between design data and CAD data.

In FIG. 5, a reference numeral 516 denotes a secondary storage device, which can store therein images stored in the memory 513. The secondary storage device 516 also can store, into the memory 513, any abnormal section found in the image capturing target area 509 being an image processing result, and the outer characteristics of the abnormal section. A reference numeral 517 denotes a computer terminal, which can display thereon the images stored in the secondary storage device 516 or the memory 513. A user can make settings of various device operations by making an input to the computer terminal 517.

In FIG. 5, a reference numeral 518 denotes an entire control system. The entire control system 518 is configured to include components under reference numerals of 521, 522, 523, 524, and 525. The component of 521 is a current amount control unit for electron beams, the component of 522 is a deflection control unit that controls over the deflectors 505 and 506, and the component of 523 denotes an electron lens intensity control unit that controls over electron lenses 502 and 503, and the objective lens 507. The component of 524 is a stage control unit that controls over the movement of a field of view as a result of the movement of an XY stage 514, and the component of 525 denotes a sequence control unit that controls over the inspection sequence in its entirety. A reference numeral 519 denotes a data input section, which is provided with coordinates of the image capturing target area 509 and CAD data for comparison with an SEM image. A reference numeral 520 denotes a data conversion section, which converts stroke data into image data for easing matching between CAD data and an SEM image.

Figure 6:
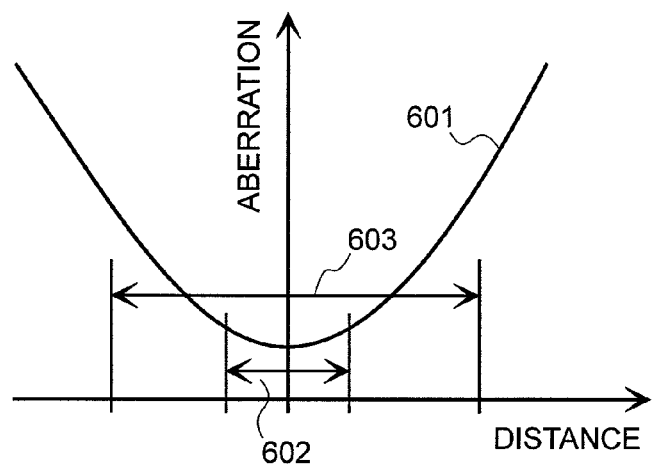
FIG. 6 is a graph showing the relationship between a distance from the center axis of an electro optical system and an aberration.

FIG. 6 shows an aberration when the electron beams 500 are used to scan the image capturing target area 509 in the electro optical system of the SEM 50 of FIG. 5. In FIG. 6, a reference numeral 601 denotes the correspondence between a distance from the center axis of the electro optical system of the SEM 50 and an aberration. The aberration is smallest on the axis, and thereat, the beam diameter is also small. The aberration is increased as the distance from the axis is increased. For inspection of any shape defect using a CD-SEM (Critical Dimension SEM: measurement SEM) or others currently in charge of inspection of hot spot portions, only an area 602 that can lead to a relatively-satisfactory resolution is used for image capturing by the SEM 50.

On the other hand, in the invention, an abnormal section is extracted in advance using a coarse resolution, and thus extracted abnormal section is subjected to image capturing with a resolution of a satisfactory level. Accordingly, in a step of extracting the abnormal section, an area 603 is used for image capturing, and only when there is any portion determined as being an abnormal section, the area 602 is used for image capturing with a high magnification.

Figure 7:
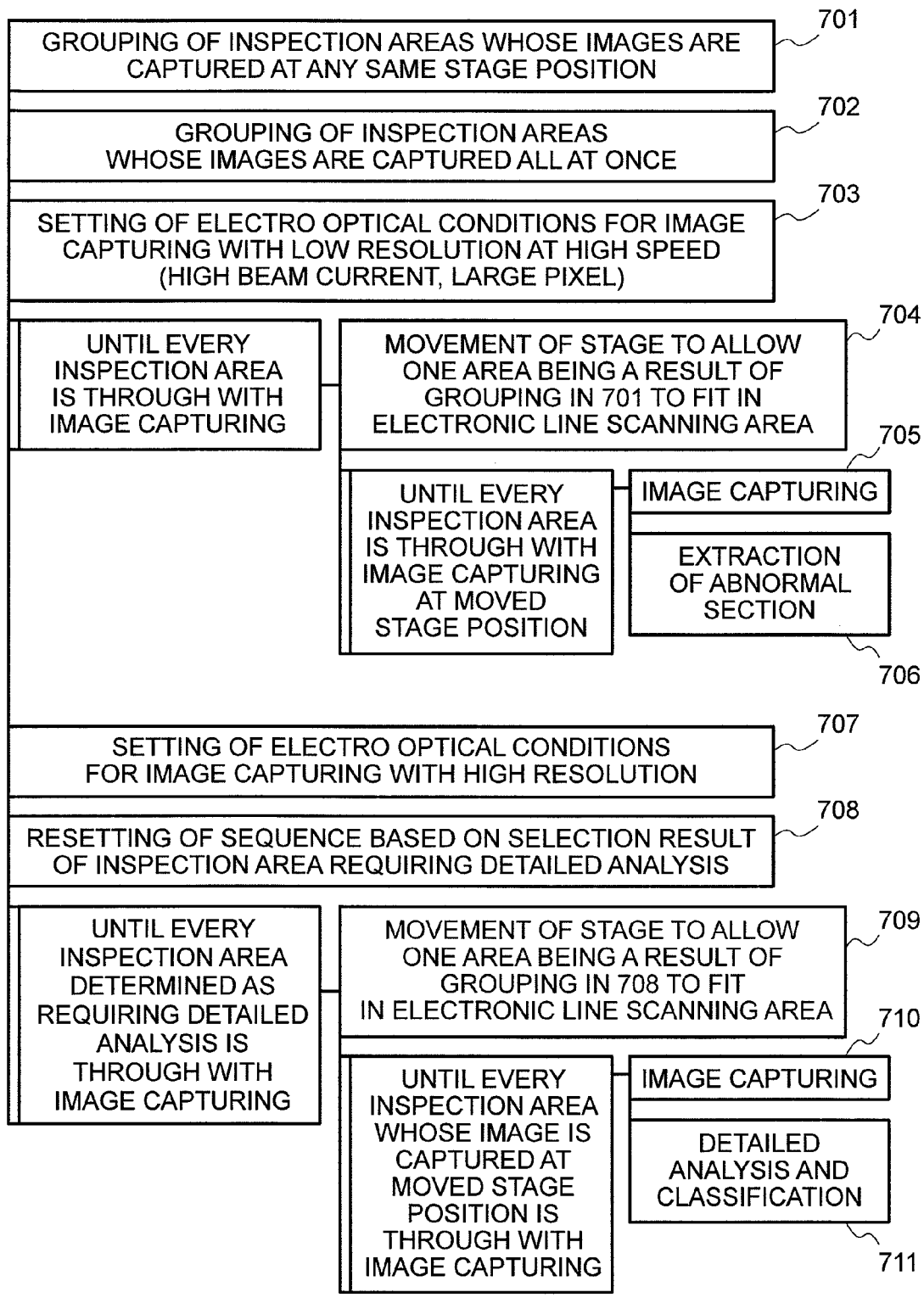
FIG. 7 is a sequence diagram showing the process procedure of defect automatic image capturing.

FIG. 7 shows an inspection sequence using the apparatus described by referring to FIG. 5. First of all, as shown in FIG. 2 or 3, grouping is performed to inspection areas whose images are captured on any same stage. Thereafter, as described by referring to FIG. 4, grouping is performed to inspection areas whose images are captured all at once. Note here that the steps of 701 and 702 are not necessarily executed in the apparatus of FIG. 5 because a setting can be automatically made if information of a lithography simulator or others determine areas for inspection. Information about grouping may be input together with an input of CAD data or coordinates of inspection areas.

Next, in the step of 703, a condition setting is made to the electro optical system to enable image capturing with a low resolution at high speed. For image capturing at high speed, a setting is made with the combination of the following conditions:

1. Increase of the amount of current of the electron beams 500 coming from the electron source 501 in the SEM 50, 2. Increase of the deflection speed in the deflectors 505 and 506, 3. Setting of scanning frequency to once or little more frequent to repeatedly scan any one specific portion of an inspection area by the deflectors 505 and 506 using the electron beams 500, and setting of addition frequency, i.e., frame addition frequency, in the addition circuit 526 to a small value, and 4. Setting of sampling frequency of the A/D converter 512 to increase the pixel size to be determined by the sampling frequency and the deflection speed in the deflectors.

In the step of 704, one of not-yet-inspected groups being the grouping results in the step of 701 is selected, and the XY stage 524 is moved to enable scanning by electron beams to every inspection area of the selected group. In the step of 705, the SEM image capturing is performed to every group of inspection areas whose images are to be captured all at once at the position on the stage, i.e., grouping results in the step of 702. In the step of 706, the resulting images are processed so that an abnormal section is extracted.

After every inspection area is subjected to image capturing, in the step of 707, a setting is made to image-capturing conditions for the electro optical system to enable image capturing with a high resolution. This is for image capturing of the abnormal section extracted in the step of 706 with a high resolution. That is, a setting is made with the combination of the following conditions almost contrary to the image-capturing conditions set in the step of 703:

1. Decrease of the amount of current of electron beams coming from the electron source 501, 2. Decrease of the deflection speed in the deflectors 505 and 506, 3. Setting of addition frequency, i.e., frame addition frequency, to a large value in the addition circuit 526 in response to repeated scanning of any one specific portion of an inspection area by the deflectors 505 and 506 using electron beams, and 4. Setting of sampling frequency with which the pixel size is decreased.

Thereafter, in the step of 708, grouping is performed similarly to the steps of 701 and 702 so that the image capturing sequence is determined. Note here that, because the current setting is made for image capturing with a high resolution, the area available for scanning by electron beams is narrowed down so that the grouping is not performed to a large number of the image capturing target areas 509. Then in the step of 709, one of the not-yet-inspected inspection groups being the grouping results in the step of 708 is selected, and the XY stage 524 is moved to allow scanning, by the electron beams 500, of every image capturing target area 509 found in the selected group. In the step of 710, SEM image capturing is then performed similarly to the step of 705, and the image captured in the step of 711 is subjected to detailed analysis and classification.

Figure 8:
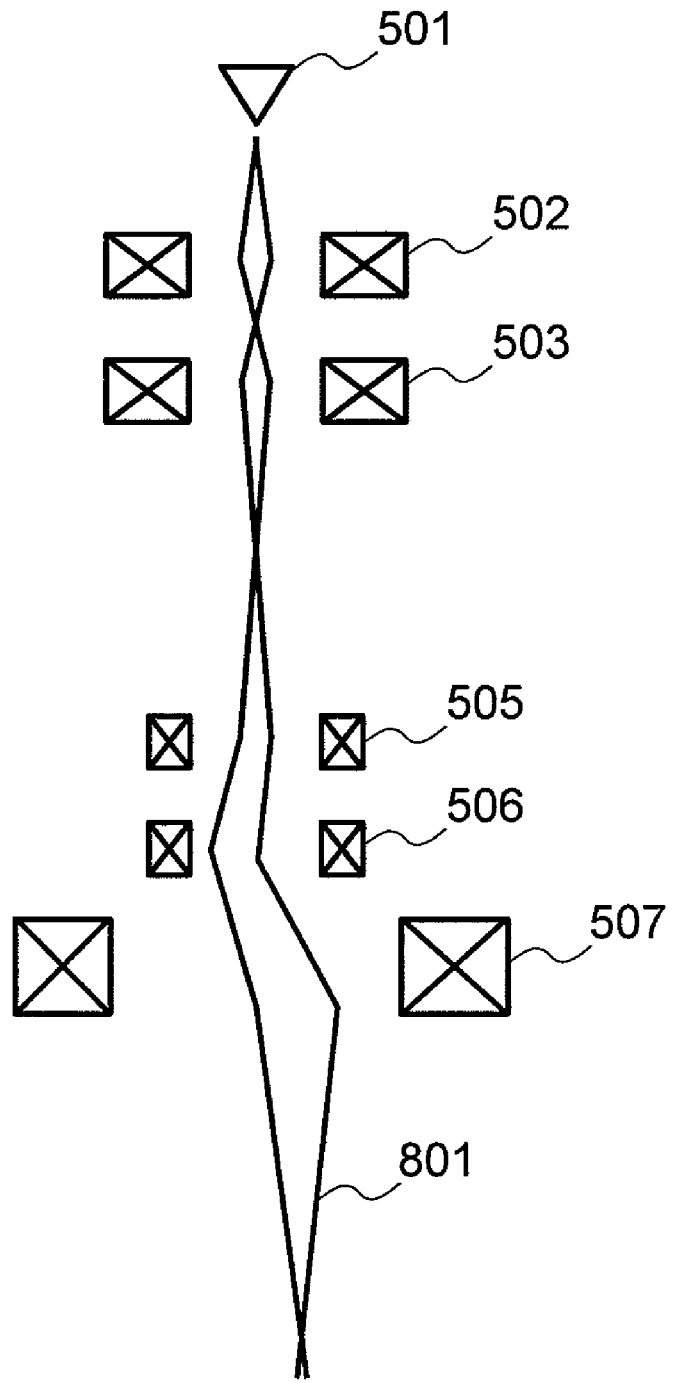
FIG. 8 is a block diagram of an electro optical system showing an exemplary electron beam path.
Figure 9:
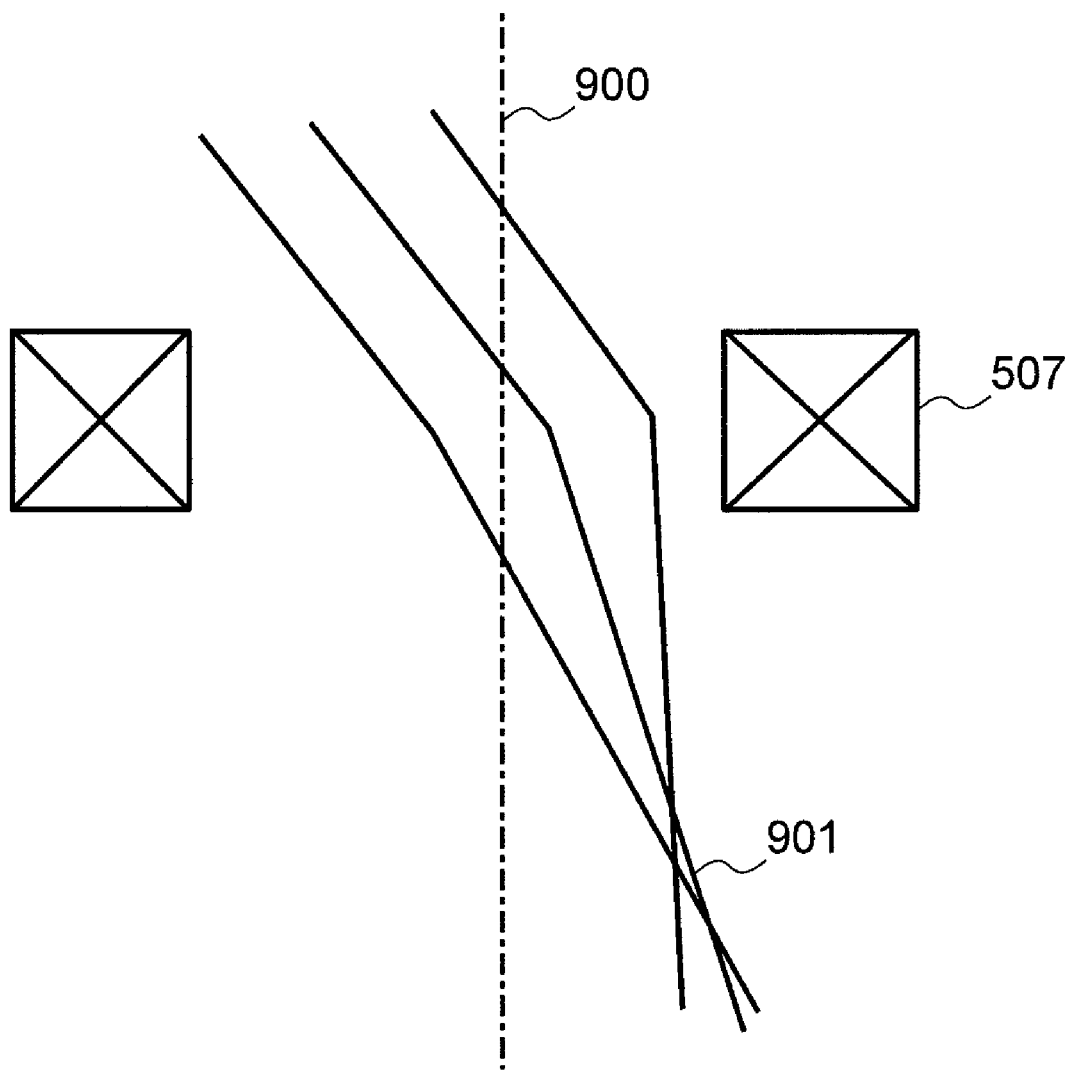
FIG. 9 is a diagram showing a part of an electro optical system for illustrating the increase of aberration when the distance is large from the center axis of the electro optical system.

FIG. 8 shows the path of the deflected electron beams 500. In the SEM 50 of the invention, the two-stage deflectors 505 and 506 are so disposed as to deflect opposite to each other, thereby reducing the aberration on the image capturing target area 509. If with a large displacement from the optical center axis of the SEM 50, as shown by 901 of FIG. 9, the electron beams 500 pass each different position of the lens, thereby causing a frame aberration or others on the image capturing target area 509 and the reduction of the resolution. This phenomenon can be solved by reducing the diameter of the electron beams 500 when entering into the objective lens 507. As to frame aberration, the aberration occurs in proportion to the square of the diameter of the electron beams 500 entering the objective lens 507. As such, by reducing the diameter of the electron beams 500 as such, the diameter of the electron beams 500 can be reduced on the inspection target area at the position away from the axis.

Figure 10:
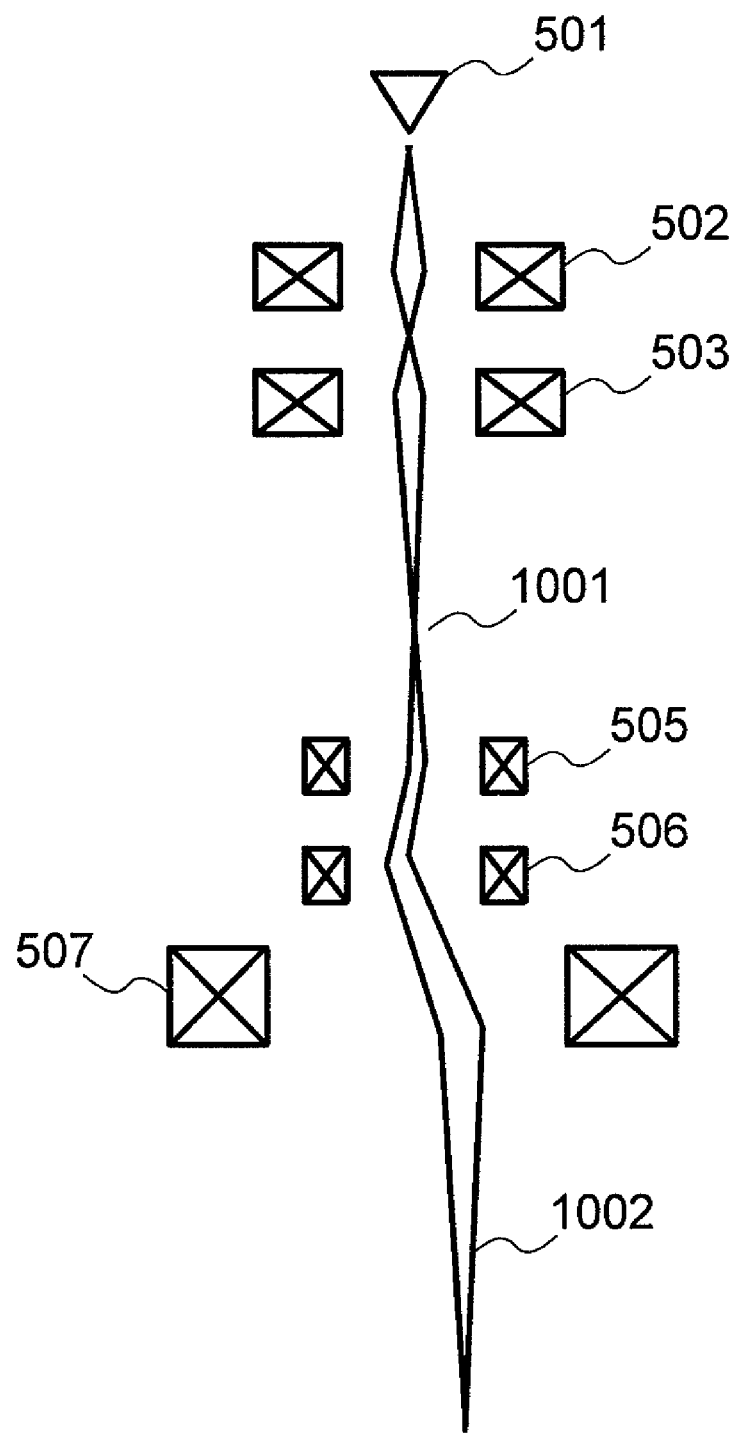
FIG. 10 is a block diagram of an electro optical system showing another exemplary electron beam path.

FIG. 10 shows the path of the electron beams 500 set as such. In FIG. 10, the magnetic field of the electron lens 503 is set weak, thereby moving a cross point 1001 closer to the objective lens 507 than the cross point of FIG. 8. At the cross point 1001, the beam diameter of the electron beams 500 is minimized on the objective lens 507.

When the electron beams 500 entering the objective lens 507 are reduced in diameter as shown in FIG. 10, two types of phenomenon occur, thereby increasing the beam diameter in the vicinity of the center axis 900 of the electro optical system. The two types of phenomenon include an increase of down-scaling factor in the objective lens 507, and an increase of diffraction aberration.

Figure 11:
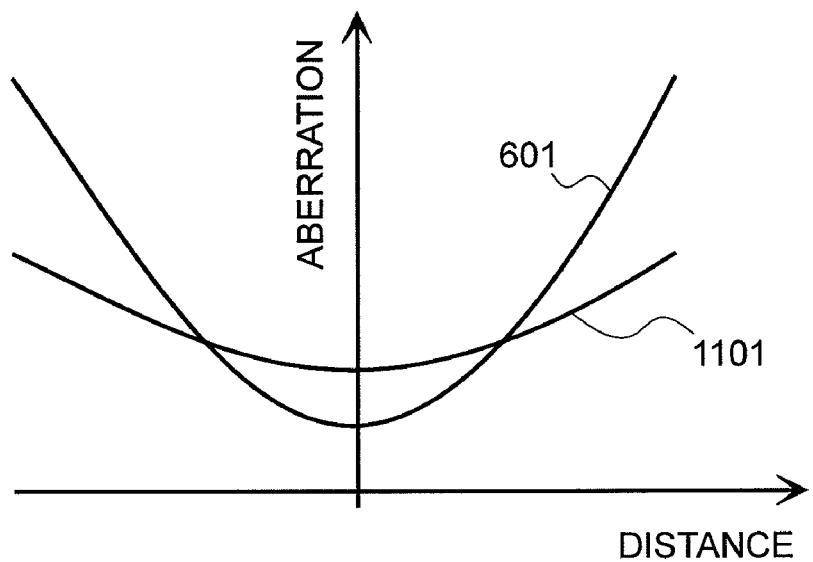
FIG. 11 is a graph showing the relationship between a distance from the center axis of an electro optical system and an aberration respectively for low- and high-resolution image capturing.

Accordingly, the correspondence between the distance from the center axis 900 of the electro optical system and the aberration looks as indicated by 1101 of FIG. 11. With the correspondence of FIG. 11, the increase of aberration is not steep compared with data 601 even at the position away from the center axis of the electro optical system so that the area available for scanning by the electron beams 500 can be increased in size. Herein, the data 601 is indicating, for reference use, the aberration characteristics in the case of FIG. 6. Moreover, the fact that the beam diameter is not increased that much at the center axis 900 and therearound in the electro optical system serves effective in view of making processing details uniform in image processing, and also in view of performing abnormal section extraction at high speed.

For image capturing at high speed, there needs to set wide the scanning interval of the electron beams 500. On the other hand, when the scanning interval is increased while the electron beams 500 being small in diameter, this causes aliasing. Assuming that the intensity profile of the electron beams 500 on the image capturing target area 509 has the Gaussian distribution, the space cutoff frequency characteristics by the electron beams 500 will also show the Gaussian distribution. As such, the space cutoff frequency shows the characteristics being inversely proportional to the diameter of the electron beams 500.

Figure 12:
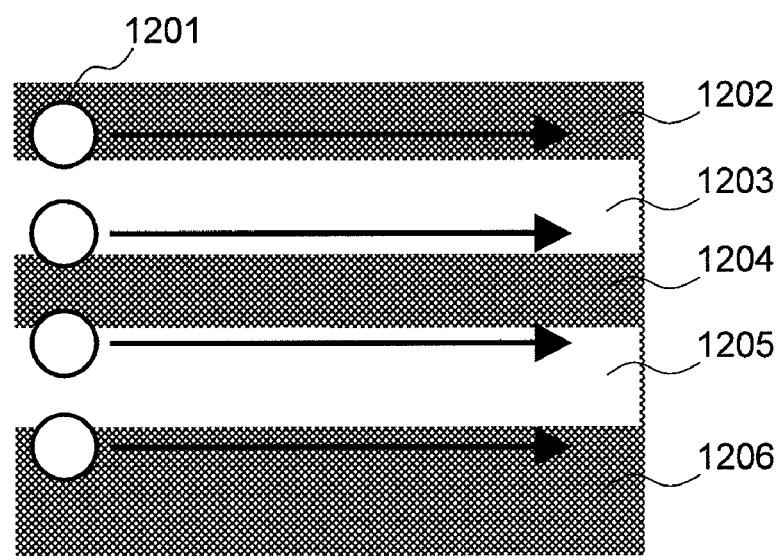
FIG. 12 is a diagram showing the relationship between an electron beam spot and an inspection target pattern for illustrating the mechanism of pseudo pattern generation when the electron beams are small in diameter.

When the cutoff frequency with such a diameter of the electron beams is high, and when the cutoff frequency exceeds a half of the sampling frequency determined by the scanning interval of the electron beams, the possibility is increased for occurrence of pseudo pattern by aliasing. FIG. 12 shows a case where the image capturing target area 509 includes a pattern of minute configuration. In FIG. 12, a reference numeral 1201 indicated by a circle shows the state that the image capturing target area 509 is irradiated with the electron beams 500, i.e., irradiation spot. Reference numerals 1202 to 1206 each show a pattern or a base in the image capturing target area 509, i.e., reference numerals 1202, 1204, and 1206 denote the base, and reference numerals 1203 and 1205 denote the pattern.

Assuming here is a case where the electron beams 500 of the beam diameter of 1201 are used to scan the area of FIG. 12 in the direction as indicated by arrows, i.e., sequentially from the top to down, repeatedly for four times. In such a case, the image of the base 1204 is not captured, thereby deriving an image of pseudo pattern different from the original.

Figure 13:
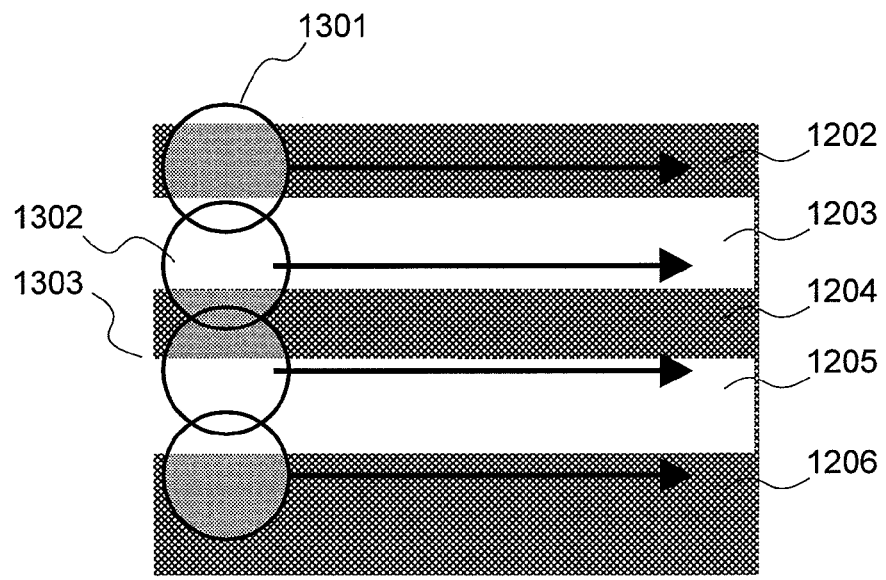
FIG. 13 is a diagram showing an exemplary electron beam scanning method with control over pseudo pattern generation, i.e., the relationship between an electron beam spot and an inspection target pattern.

On the other hand, when the electron beams 500 of the beam diameter of 1301 of FIG. 13 are used for scanning of the same area as FIG. 12, the image of the area including the area 1204 is captured with the brightness information so that no pseudo pattern is generated.

As such, at the time of high-speed image capturing with the wider scanning interval of the electron beams 500, it is required to increase the beam diameter at the center axis 900 of the electro optical system depending on the scanning interval. In consideration thereof, it is considered advantageous if the optical system is set as shown in FIG. 10, and in the step of 703 in the inspection sequence of FIG. 7, such a setting is desirably included in the setting conditions.

Figure 14:
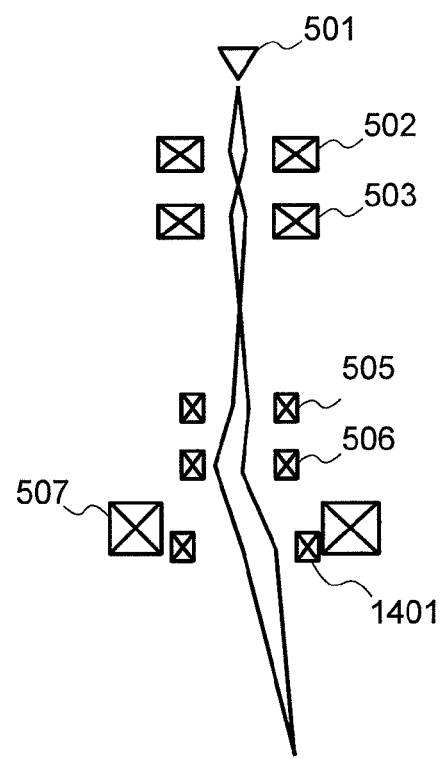
FIG. 14 is a block diagram of an electro optical system showing an exemplary placement of deflectors in an electro optical system.
Figure 15:
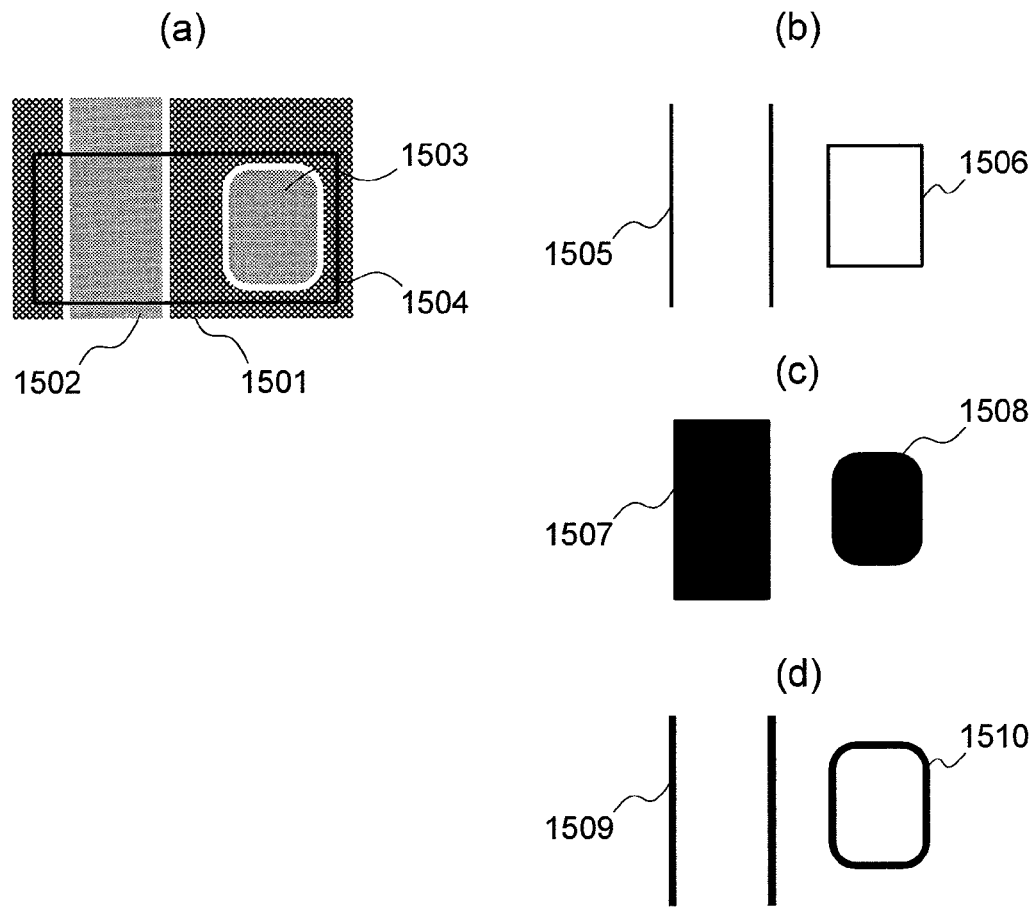
FIG. 15A is a plan view of an inspection target pattern.
FIG. 15B is a diagram showing the outline of an inspection target pattern derived from design data.
FIG. 15C is a plan view of a pattern having rounded corners as a result of image processing of design data.
FIG. 15D is a diagram created from outline information derived from the pattern of FIG. 15C.

Described next is the configuration of FIG. 14, i.e., modified example of the electro optical system. With the electro optical system of FIG. 14, unlike the system of FIG. 5, a third deflector 1401 is disposed inside or below the objective lens 507. FIG. 14 shows an exemplary placement in which the third deflector 1401 is disposed inside of the objective lens 507.

To increase more the area available for scanning by the electron beams 500 with respect to the electro optical system of FIG. 5, the electron beams 500 are to be deflected in the direction opposite to the force of bending the electron beams 500 toward the center of the optical axis of the objective lens 507. This is aimed not to cause a large angle change to the electron beams 500 in the objective lens 507. Note here that, if this is the case, the electron beams 500 are not allowed to come from the direction of normal with respect to the inspection target, and thus the deflection is performed in the acceptable range. Because this deflector 1401 is disposed inside or below the objective lens 507, it is required to form a magnetic or electronic field larger than that of the deflectors 505 and 506 with respect to the electron beams 500, thereby not being able to perform deflection at high speed. As such, for deflection by the deflector 1401, a value setting is so made as to allow deflection only before starting of image capturing in the step 705 of the sequence of FIG. 7, and the deflectors 505 and 506 are put in charge to control the scanning by the electron beams 500 in the step of 705.

Described next is a process of extracting an abnormal section to be executed in the step of 706 in FIG. 7. In FIG. 15A, a reference numeral 1501 denotes an image acquired by an SEM, and therein, an area 1504 including border portions 1502 and 1503 is an area used for determining, by image processing, whether there is any abnormal section. The corresponding CAD data is patterns 1505 and 1506 shown in FIG. 15B, and is described by a bending line in the form of rectangular. As such, the corner portions thereof look especially different from the actual SEM image. If such CAD data is used as it is for comparison with an SEM image, the corner portions may be determined as defects.

In consideration thereof, in the invention, first of all, a pattern approximated by a bending line is changed to a binary image being solid-filled on a pattern basis. The binary image is filtered by an isotropic function such as gauss, and then changed to a binary image again. As a result, the pattern will have rounded corner portions as shown by 1507 and 1508 in FIG. 15C. Thereafter, the border position is defined between the patterns 1507 and 1508 so that such edge images 1509 and 1510 as shown in FIG. 15D are derived. A search is then made in the vicinity of the edge images to find an edge on the SEM image of FIG. 15A in the same direction as the edge of the edge image for every position. Another search is also made on the CAD corresponding to the large-intensity edge on the SEM image. The resulting correspondences are used for extraction of any shape change, generation of pattern that is not originally existed, elimination of pattern, and breaking of pattern.

The issue at this time is the reliability of the shape of the corner portions on the CAD data formed by a bending line. In this invention, filtering is performed using an isotropic function such as gauss so that the resulting pattern looks similar to the SEM image. However, this filtering function is not necessarily the same for every process, and varies depending on the shape, whereby there is a possibility of not being the same as the actual SEM image.

In consideration thereof, in the invention, a threshold value for use to extract an abnormal section is changed depending on the area. The approximation using the filtering function is known to show the relatively good accuracy for the linear pattern, and show the relatively poor accuracy at the corner portions and line ends. In these portions, the distance is long between the line portion of the original CAD data and the edge portion of the pattern as a result of approximation by filtering. As such, the reference for abnormality determination is calculated by comparison between the approximated pattern and the shape of the original CAD data.

Figure 16:
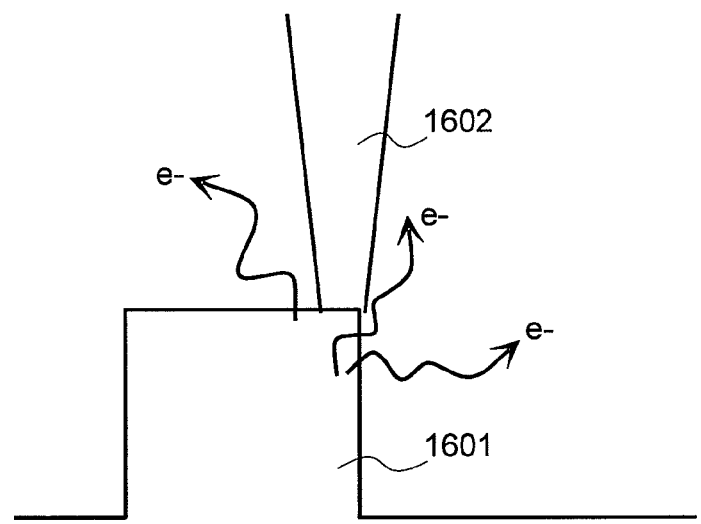
FIG. 16 is a cross-sectional enlarged view of a pattern for illustrating the increase of brightness in an SEM image at an edge section.

Another problem for extraction of an abnormal section with such a method is the brightness reduction in the edge portion in the SEM image when image detection is made with a relatively large pixel size and a large beam diameter. When a stereoscopic pattern as indicated by 1601 of FIG. 16 is irradiated with electron beams 1602, the electron beams 1602 generate secondary electrons while entering inside of the pattern 1601. For detection of secondary electrons by a detector, the secondary electrons generated inside of the inspection target have to be emitted outside of the pattern. At the pattern edge, compared with a plane portion, the distance is short from the portion where the secondary electrons are generated to the outside so that the possibility for the detector to detect the secondary electrons generated at the pattern edge is increased, thereby being able to detect an edge being enhanced.

The concern here is that, when the beam diameter is increased, the ratio of the secondary electrons to be emitted from the edge portion is reduced with respect to the entire secondary electrons generated as a result of beam irradiation. As a result, the ratio of the brightness increase is reduced in the pattern edge portion, thereby resulting in a difficulty in stable edge detection by image processing.

Second Embodiment

In the first embodiment, at the time of image detection with a relatively large pixel size and a large beam diameter, if this beam diameter becomes larger, the ratio of the secondary electrons to be emitted from the edge section is reduced with respect to the entire secondary electrons generated as a result of beam irradiation. As a result, the increase ratio of the brightness in the pattern edge portion is reduced, thereby resulting in a difficulty in stable edge detection by image processing.

For such a problem, detecting the secondary electrons or reflecting electrons to be generated as a result of irradiation of electron beams is considered effective using various types of detectors depending on the direction coming from an image capturing target. Described below is means for solving such a problem as a second embodiment.

Figure 17:
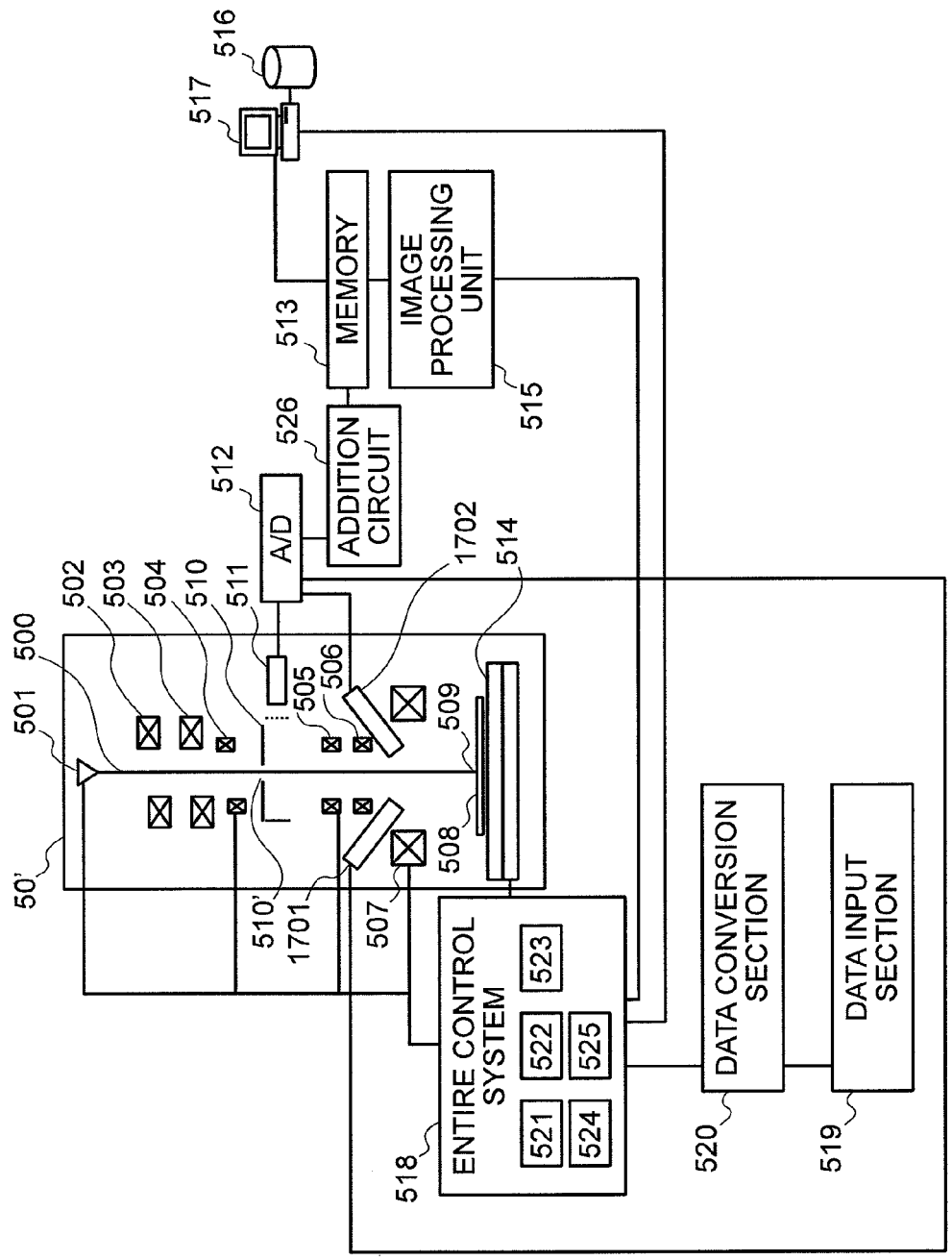
FIG. 17 is a block diagram showing the schematic configuration of an inspection device in its entirety in a second embodiment.
Figure 18:
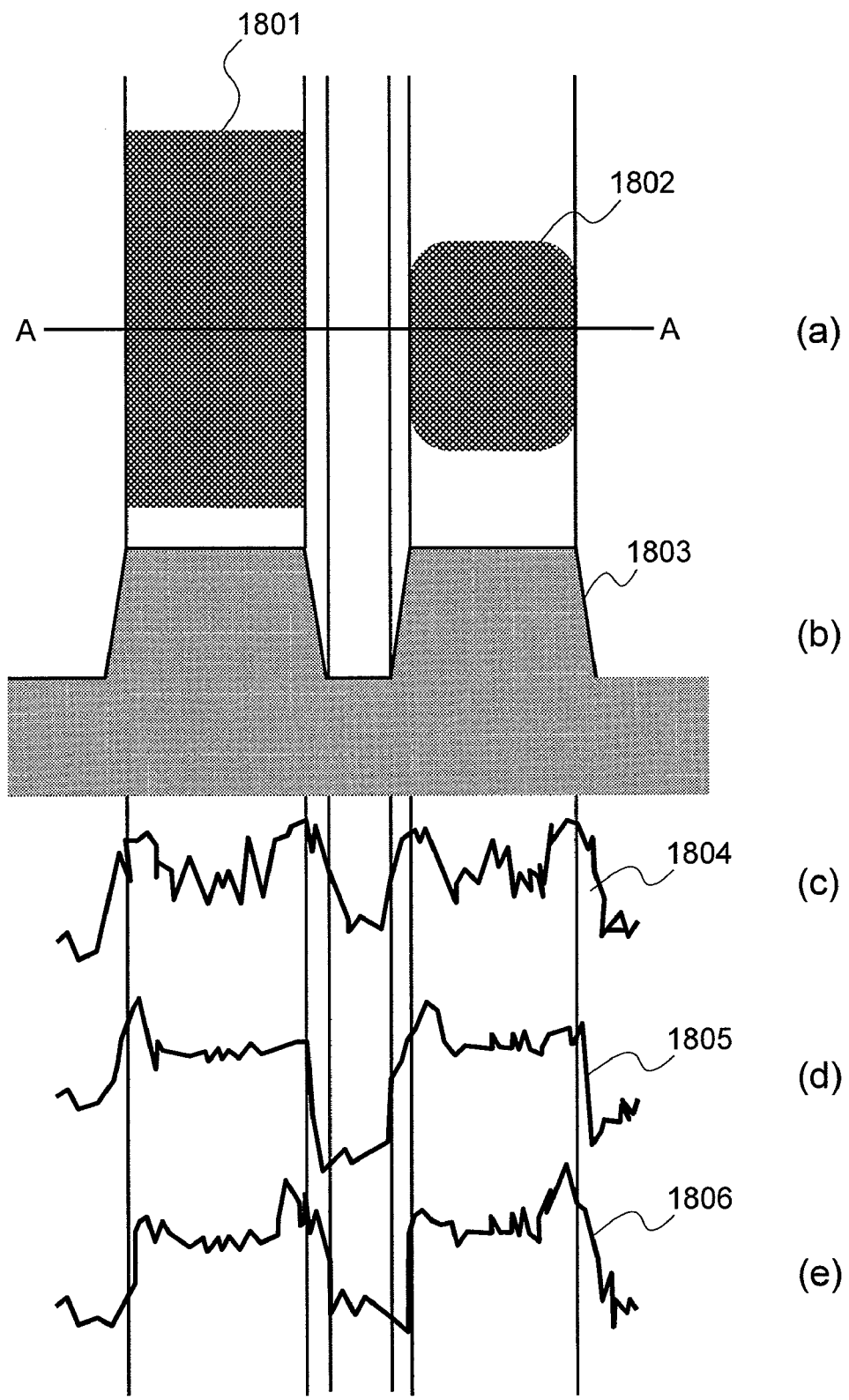
FIG. 18A is a plan view of an inspection target pattern.
FIG. 18B is a cross sectional view of the inspection target pattern.
FIG. 18C is a signal waveform diagram of a signal to be detected by a detector 511 at the time of scanning of the inspection target pattern using electron beams.
FIG. 18D is a signal waveform diagram of a signal to be detected by a detector 1701 at the time of scanning of the inspection target pattern using electron beams.
FIG. 18E is a signal waveform diagram of a signal to be detected by a detector 1702 at the time of scanning of the inspection target pattern using electron beams.
Figure 20:
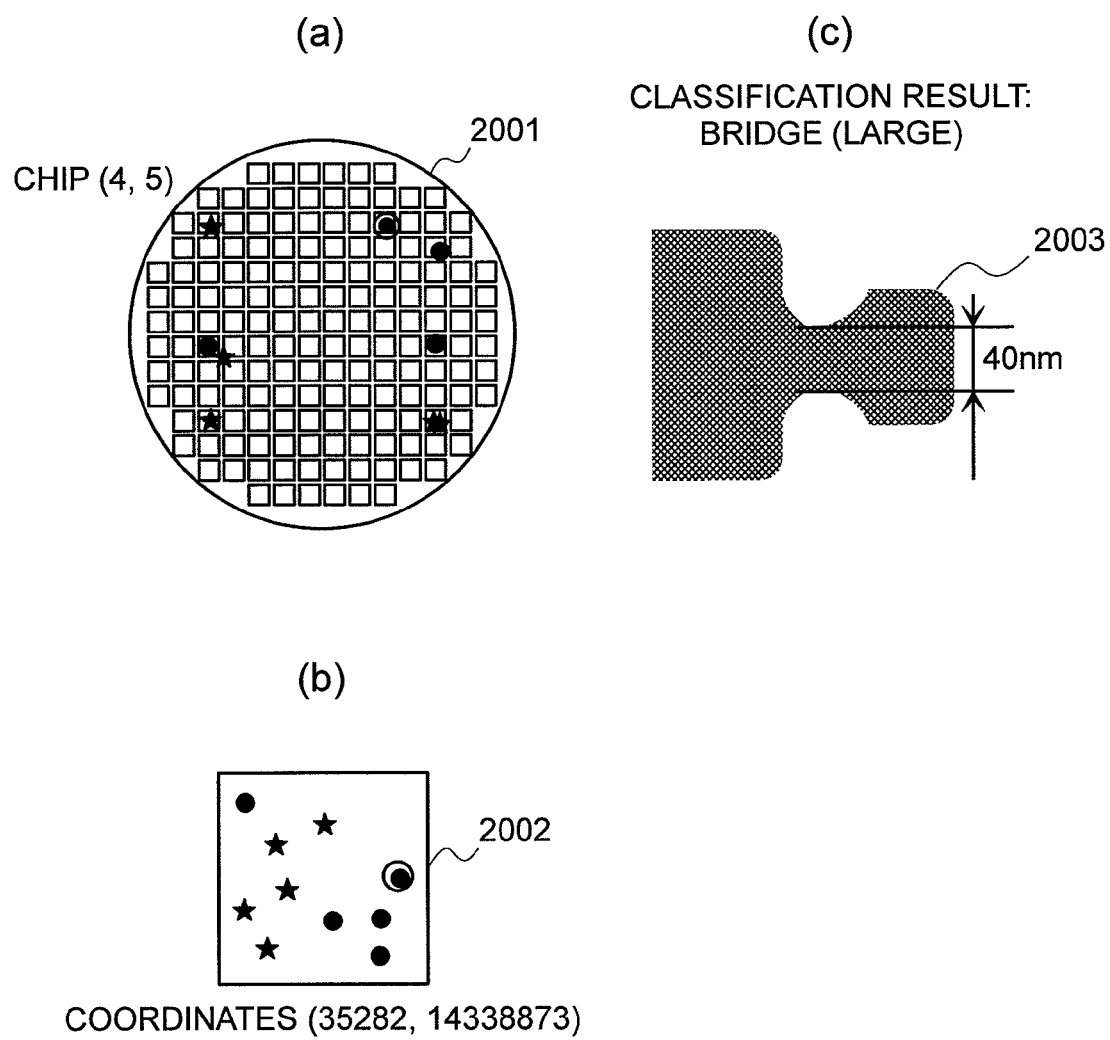
FIG. 20A is a front view of a display screen displaying thereon the classification result, i.e., distribution of an abnormal section in the form of a wafer map.
FIG. 20B is a front view of the display screen displaying thereon the classification result, i.e., distribution of an abnormal section in a semiconductor chip.
FIG. 20C is a front view of the display screen showing an SEM image of the abnormal section.

The configuration of FIG. 17 is almost the same as that of FIG. 5, but a difference lies in that two detectors 1701 and 1702 are provided. The detectors 1701 and 1702 each detect, from electrons coming from an inspection target, any electrons emitted with an angle from the center axis 900 of an SEM, and forward the detection result to the A/D converter 512. Such an input of electrons is added together by the addition circuit 526 every time scanning is performed at any same position, and the memory 513 separately goes through image accumulation. The images are then subjected to image processing in the image processing unit 515 so that an abnormal section can be extracted.

FIGS. 18A to 18E each show a brightness change of a pattern whose image is captured by the detectors 511, 1701, and 1702. In FIG. 18A, reference numerals 1801 and 1802 each denote a plan view of a pattern, and in FIG. 18B, a reference numeral 1803 denotes the cross-sectional profile cut along a line A-A. The pattern of such a cross-sectional profile is irradiated with the electron beams 500, and the resulting brightness profiles of the electrons detected by the detectors 511, 1701, and 1702 are denoted by 1804, 1805, and 1806, respectively.

With the size increase of the beam profile, a signal to be detected by the detector 511 hardly shows the edge effects with which the portion of a pattern edge brightly glows. This phenomenon becomes more apparent, and the edge effects are not observed that much when an inspection target is a resist, for example. This is because, when the acceleration voltage is set low to the electron beams for suppressing any possible shape change by the electron beams, the area of generating the secondary electrons in the inspection target is reduced in size.

On the other hand, with the brightness profiles 1805 and 1806 derived by detecting the electrons emitted in the diagonal direction by the detectors 1701 and 1702, the electrons with relatively higher energy are to be detected. As such, therewith, the edge effects are hardly observed compared with the brightness profile 1804 being a detection result by the detector 511. However, with a pattern whose wiring is higher than the recent wiring distance, i.e., pattern with higher aspect ratio, electrons to be diagonally emitted by electron beams irradiated between the wiring collide against any adjacent pattern, and thus are not detected. As such, the base portion is detected with the darkness compared with the portion above the wiring. This thus enables to determine that the dark portion is the base, and the bright portion is the pattern.

Note that, when only the two detectors are disposed opposing each other as the detectors 1701 and 1702, the base is not detected with darkness if there is no pattern in the direction of electron detection for the detectors 1701 and 1702, thereby resulting in a difficulty in detecting the wiring edge. As such, the pattern detection can be performed with stability by complementarily using the image detected by the detectors 511, 1701, and 1702, and similarly to the method described in the first embodiment, an abnormal section is extracted by comparison with CAD data.

After an abnormal section is extracted, a setting is made for image capturing with a high resolution in the step of 707, and then an image with a high resolution is captured. Then in the step of 711, the image is analyzed and classified. In this example, based on an image captured with a high resolution, a comparison is made with CAD data so that any shape change is detected, and any dimension change is output and classified. This classification is performed as shown in FIGS. 19A to 19G, for example. Compared with a normal pattern 1901 of FIG. 19A, FIG. 19B shows a thick pattern 1902, FIG. 19C shows a thin pattern 1903, FIG. 19D shows a thin bridge 1904, FIG. 19E shows a thick bridge 1905, FIG. 19F shows a broken pattern 1906, and FIG. 19G shows a foreign substance 1907.

The classification result is displayed on the terminal 517, and recorded to the storage device 516. For the classification result, a selection of method of dimension measurement is made depending on the type. For example, displayed is the measurement result for a user to pay attention for every type of abnormality, i.e., the thick pattern 1902 of FIG. 19B and the thin pattern 1903 of FIG. 19C show the width increase or decrease from the pattern width that is supposed to be, the thin bridge 1904 of FIG. 19D and the thick bridge 1905 of FIG. 19E show the bridge width, the broken pattern 1906 of FIG. 19F shows the broken width, and the foreign substance 1907 of FIG. 19G shows the projection length of the foreign substance in the X and Y directions.

FIGS. 20A to 20C show the display screen of the computer terminal 517 displaying thereon the classification result and the dimension measurement result. In FIG. 20A, a reference numeral 2001 denotes a wafer map, and any extracted abnormal section is indicated by each different color or mark for every classification result. In FIG. 20B, a reference numeral 2002 shows the distribution state of an abnormal section in a semiconductor chip, and similarly to the wafer map 2001 of FIG. 20A, a marking is applied for every classification result. In FIG. 20A, the wafer map 2001 includes therein a chip of the selected abnormal section, and in FIG. 20B, the semiconductor chip 2002 includes the coordinates in the chip. The captured image is displayed as indicated by 2003 of FIG. 20C, and displayed thereon is the dimension measured for the abnormal section and the classification result.

In this invention, an inspection area is assumed as often suffering from defects found by a lithography simulator. This is surely not restrictive, and an inspection area can be alternatively determined. A possible inspection area includes, for example, an area showing the high possibility of causing defects such as a cell portion in the vicinity of a cell boundary of a memory cell formed in the vicinity of the wafer, or a point that has been suffered from a systematic defect in the past or a point where the wiring density of the lower layer is high, and the amount of cutting is increased as a result of CMP.

The invention may be embodies in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect review method for a semiconductor device, comprising the steps of:
   grouping a plurality of reviewing inspection areas on an inspection target sample;
   capturing an image of each of the reviewing inspection areas grouped using a scanning electron microscope being under first image-capturing conditions, and acquiring a plurality of images of the reviewing inspection areas with a first magnification;
   extracting an abnormal section from the acquired images of the inspection areas by comparison with design data; and
   capturing an image of the extracted abnormal section using the scanning electron microscope being under second image-capturing conditions, and acquiring an image of the extracted abnormal section with a second magnification being higher than the first magnification.

2. The defect review method for the semiconductor device according to claim 1, wherein
   in the step of grouping the inspection areas, first grouping is performed to the inspection areas on the inspection target sample to allow all of the inspection areas to fit in an electron beam scanning range of the scanning electron microscope in charge of capturing an image of the inspection target sample, and second grouping is performed to an inspection area group being a result of the first grouping for simultaneous image capturing using the scanning electron microscope, and
   in the step of acquiring the images with the first magnification, the inspection area group through with the second grouping is subjected to image capturing using the scanning electron microscope being under the first image-capturing conditions.

3. The defect review method for the semiconductor device according to claim 1, wherein
   in the scanning electron microscope being under the first image-capturing conditions, electron beams have an amount of current larger than an amount of current in electron beams in the scanning electron microscope being under the second image-capturing conditions.

4. The defect review method for the semiconductor device according to claim 3, wherein
   in the scanning electron microscope being under the first image-capturing conditions, electron beams have an amount of current larger than an amount of current in electron beams of the scanning electron microscope being under the second image-capturing conditions.

5. The defect review method for the semiconductor device according to claim 3, wherein
   in the scanning electron microscope being under the first image-capturing conditions, a time to be taken for image capturing of a pixel is shorter than a time to be taken for image capturing of a pixel in the scanning electron microscope being under the second image-capturing conditions.

6. The defect review method for the semiconductor device according to claim 1, wherein
   in the scanning electron microscope being under the first image-capturing conditions, a time to be taken for image capturing of a pixel is shorter than a time to be taken for image capturing of a pixel in the scanning electron microscope being under the second image-capturing conditions.

7. A defect review method for a semiconductor device, comprising the steps of:
   capturing images of a plurality of reviewing inspection areas on an inspection target sample to allow all of the inspection areas to fit in an electronic line scanning range of a scanning electron microscope being under first image-capturing conditions, and acquiring a plurality of images of the reviewing inspection areas;
   extracting, by comparison with design data, an abnormal section from the images of the inspection areas acquired by image capturing with the first image-capturing conditions; and
   capturing an image of the extracted abnormal section using the scanning electron microscope being under second image-capturing conditions, and acquiring an image of the abnormal section.

8. A defect review method for a semiconductor device, comprising the steps of:
   fitting a plurality of inspection areas on an inspection target sample in an electronic line scanning range of a scanning electron microscope, and capturing an image of each of the inspection areas with first image-capturing conditions;
   extracting, by comparison with design data, an abnormal section from the images of the inspection areas acquired by image capturing with the first image-capturing conditions;
   capturing an image of the extracted abnormal section using the scanning electron microscope being under second image-capturing conditions;

classifying the image of the abnormal section being a result of image capturing with the second image-capturing conditions based on a result of comparison with the design data;

measuring a size of a portion preset for every type of classification based on a result of classification; and displaying the result of classification and a result of size measurement together with the captured images.

9. The defect review method for the semiconductor device according to claim 8, wherein in the scanning electron microscope being under the first image-capturing conditions, electron beams have an amount of current larger than an amount of current in electron beams of the scanning electron microscope being under the second image-capturing conditions.

10. The defect review method for the semiconductor device according to claim 8, wherein in the scanning electron microscope being under the first image-capturing conditions, a time to be taken for image capturing of a pixel is shorter than a time to be taken for image capturing of a pixel in the scanning electron microscope being under the second image-capturing conditions.

11. A defect review apparatus for a semiconductor device, comprising:

a scanning electron microscope provided with a table that is allowed to move in a plane with an inspection target sample placed thereon;

image-capturing condition setting means for setting image-capturing conditions for reviewing the inspection target sample using the scanning electron microscope;

table control means for controlling the table of the scanning electron microscope to allow a plurality of reviewing inspection areas on the inspection target sample to fit in an image capturing area of the scanning electron microscope being under first image-capturing conditions set by the image-capturing condition setting means;

first image processing means for extracting, by comparison with design data, an abnormal section from images of the inspection areas acquired by the scanning electron microscope being under the first image-capturing conditions set by the image-capturing condition setting means; and second image processing means for processing an image of the extracted abnormal section in a state that the scanning electron microscope is set with second image-capturing conditions by the image-capturing condition setting means.

12. The defect review apparatus for the semiconductor device according to claim 11, wherein the image-capturing condition setting means performs first grouping to the inspection areas on the inspection target sample to allow all of the inspection areas to fit in an electron beam scanning range of the scanning electron microscope in charge of image capturing of the inspection target sample, and performs second grouping to an inspection area group being a result of the first grouping for simultaneous image capturing using the scanning electron microscope, and the first image processing means processes an image of the inspection area group through with the second grouping using the scanning electron microscope being under the first image-capturing conditions.

13. The defect review apparatus for the semiconductor device according to claim 11, wherein the image-capturing condition setting means sets an amount of current in the scanning electron microscope being under the first image-capturing conditions larger than an amount of current in the electron beams of the scanning electron microscope being under the second image-capturing conditions.

14. A defect review apparatus for a semiconductor device, comprising:

scanning electron microscope means;

image-capturing condition setting means for setting image-capturing conditions for reviewing an inspection target sample using the scanning electron microscope means;

first image processing means for extracting, by comparison with design data, an abnormal section from images of a plurality of inspection areas on the inspection target sample acquired in a state that the scanning electron microscope means is set with first image-capturing conditions by the image-capturing condition setting means; and second image processing means for processing an image of the abnormal section extracted by the first image processing means in a state that the scanning electron microscope means is set with second image-capturing conditions by the image-capturing condition setting means, and measuring a size of a portion preset for every type of classification based on a classification result of the abnormal section.

15. The defect review apparatus for the semiconductor device according to claim 14, wherein the image-capturing condition setting means performs first grouping to the inspection areas on the inspection target sample to allow all of the inspection areas to fit in an electron beam scanning range of the scanning electron microscope in charge of image capturing of the inspection target sample, and performs second grouping to an inspection area group being a result of the first grouping for simultaneous image capturing using the scanning electron microscope, and the first image processing means processes an image of the inspection area group through with the second grouping using the scanning electron microscope being under the first image-capturing conditions.

16. The defect review apparatus for the semiconductor device according to claim 14, wherein the image-capturing condition setting means sets an amount of current in the scanning electron microscope being under the first image-capturing conditions larger than an amount of current in electron beams of the scanning electron microscope being under the second image-capturing conditions.

* * * * *